US00RE35779E

United States Patent [19]

Alferness et al.

[11] E Patent Number: Re. 35,779

[45] Reissued Date of Patent: Apr. 28, 1998

[54] POST-HEART SURGERY CARDIOVERTING SYSTEM AND METHOD

[75] Inventors: Clifton A. Alferness; Gregory M. Ayers, both of Redmond, Wash.; Jerry C. Griffin, Chicago, Ill.; Kenneth R. Infinger, Issaquah, Wash.

[73] Assignee: InControl, Inc., Redmond, Wash.

[21] Appl. No.: 608,410

[22] Filed: Feb. 28, 1996

Related U.S. Patent Documents

Reissue of:

[64] Patent No.: 5,403,353
Issued: Apr. 4, 1995
Appl. No.: 100,492
Filed: Jul. 30, 1993

[51] Int. Cl.[6] ..... A61N 1/36

[52] U.S. Cl. ..... 607/5; 607/10

[58] Field of Search ..... 607/4, 5, 6, 7, 607/8, 10

[56] References Cited

U.S. PATENT DOCUMENTS 3,474,791 10/1969 Bentov ..... 607/132
3,807,411 4/1974 Harris et al. ..... 607/10
5,190,052 3/1993 Schroeppel ..... 607/123

OTHER PUBLICATIONS

Dr. K. Westermann, 'A New External Pacemaker' Medicamundi, vol. 21, No. 2, 1976, pp. 91–94.

*Primary Examiner*—William E. Kamm
*Assistant Examiner*—Scott M. Getzow
*Attorney, Agent, or Firm*—Richard O. Gray, Jr.

[57] ABSTRACT

A post-surgical cardioverting system and method applies cardioverting electrical energy to the atria of the heart of a post-surgical heart patient. The system includes a first lead including a first elongated electrode having a proximal end and a distal end, a second lead including a second elongated electrode having a proximal end and a distal end, and sutures for releasably anchoring the distal ends of the first and second electrodes to the pericardium and disposing the first and second electrodes along the pericardium overlying the right and left atria respectively. A non-implantable cardioverter is coupled to the first and second leads for applying the cardioverting electrical energy to the first and second electrodes. When cardioversion is no longer required, the first and second leads may be pulled out of the patient's chest.

51 Claims, 2 Drawing Sheets

POST-HEART SURGERY CARDIOVERTING SYSTEM AND METHOD

Matter enclosed in heavy brackets [ ] appears in the original patent but forms no part of this reissue specification; matter printed in italics indicates the additions made by reissue.

BACKGROUND OF THE INVENTION

The present invention is generally directed to a cardioverting system and method for providing temporary cardioversion of the heart of a heart surgery patient following a heart surgery procedure. The present invention is more particularly directed to such a system and method for providing post-surgery cardioversion of the atria of the heart.

There are approximately four hundred thousand (400,000) heart surgery procedures performed annually in the United States. The types of such surgical procedures vary from coronary artery bypass grafts to valve replacements, to repair of congenital heart defects. In order to gain access to the heart, these surgeries require the chest to be opened in the middle of the sternum. An incision is then made in the pericardial sac (pericardium) to expose the heart and permit the required surgical procedure to be performed. Following the surgical procedure, the pericardial incision is reapproximated (closed except for a drain opening) with sutures and the chest cavity is closed.

Often, following such heart surgical procedures, the patients' hearts during recovery experience bradycardia or slow heart rates. In the prior art, to overcome such maladies, the hearts of post-surgical heart patients are temporarily paced for a few days following surgery, when required, to maintain the heart rates at a normal rate. This is accomplished by releasably attaching heart wires to the heart before the pericardium is sutured and the chest cavity is closed. First and second heart wires are attached to the myocardium of one of the ventricles such as the left ventricle. The heart wires are then brought outside of the chest. Thereafter, the pericardium is sutured and the chest cavity is closed. The proximal ends of the heart wires are then coupled to a temporary pacemaker to permit the heart to be paced. After the patient has recovered sufficiently wherein pacing is no longer required, the heart wires are pulled out of the patient.

Unfortunately, twenty to thirty percent of all heart surgical patients experience an arrhythmia called atrial fibrillation during the immediate or early post-surgical period. When this occurs, the heart beats rapidly and irregularly. According to reports, this constitutes a major clinical problem resulting in hypotension, heart failure, pneumonia and/or stroke, due to thromboembolism. Hence, such a condition is of great concern to the physician and it is therefore in the best interest of the patient to terminate this arrhythmia as soon as possible.

The development of post-surgical atrial fibrillation has not been associated with preoperative or postoperative events. Further, the specificity and sensitivity of age and other possible relevant factors for prediction of atrial fibrillation after heart surgery is low. No effective prophylactic regimen has yet been established.

When atrial fibrillation of a surgical patient's heart occurs during surgery, the physician terminates the fibrillation by cardioverting the heart. In this cardioversion procedure, the physician contacts each atria with a spoon-sized conductive paddle which is coupled to an external defibrillator. The external defibrillator includes a storage capacitor which is charged to a selected voltage. When the storage capacitor is fully charged, the stored energy is discharged into the atria of the heart through the paddles.

While the above-mentioned cardioverting process is very effective in terminating atrial fibrillation occurring during surgery, this procedure is not available to the physician for terminating atrial fibrillation occurring after the heart surgery is completed and the patient's chest cavity has been closed. It has been observed that the peak incidence of atrial fibrillation is during the second or third postoperative day. While external cardioversion is an option, because the patient's chest cavity at this time is closed, much larger paddles and much greater cardioverting energies must be used as compared to the paddle size and cardioverting energies employed during surgery. Such energies, generally between 50 and 360 joules, would also require that the patient be briefly anesthetized or very heavily sedated prior to attempted external cardioversion. Hence, while external cardioversion, using much larger paddles and much higher cardioverting energies, is available to the physician as an option, most physicians are reluctant to use such external cardioversion because of the likely trauma and tissue damage it would cause the patient during a time in which the patient is in initial recovery from serious open heart surgery.

Drug therapy is also an available option. Its use however is often attended with significant side effects. In addition, there is a substantial potential interaction of such drugs with the many different types and amounts of other drugs the patient is already being given during this initial recovery period.

Hence, there remains a long felt need in the art for a cardioverting system and method capable of arresting fibrillation, such as atrial fibrillation, occurring during the post-heart surgery period. More specifically, there is a need in the art for such a system and method which does not cause prolongation of the patient's recovery period due to trauma and tissue damage and which avoids the need for drug therapy to treat such a condition.

SUMMARY OF THE INVENTION

The present invention therefore provides a post-surgical cardioverting system for applying cardioverting electrical energy to the heart of a post-surgical heart patient. The system includes a first lead including a first elongated electrode having a proximal end and a distal end, a second lead including a second elongated electrode having a proximal end and a distal end, and first anchor means for releasably anchoring the distal ends of the first and second electrodes to body tissue external to but in close proximity to the heart beneath the skin of the patient to dispose the first and second electrodes in electrical contact with the heart. The system further includes a non-implantable cardiovertor coupled to the first and second leads for applying the cardioverting electrical energy to the first and second electrodes.

The present invention further provides a method of cardioverting the heart of a heart surgery patient subsequent to a heart surgery procedure. The method includes the steps of providing a first lead having a first elongated electrode and a second lead having a second elongated electrode, the first and second electrodes each having a distal end and a proximal end. The method further includes the steps of, following the heart surgery procedure and before closing the chest of the patient, releasably anchoring the distal ends of the first and second electrodes to body tissue external to but in close proximity to the heart beneath the skin of the patient to dispose the first and second electrodes in electrical contact with the heart. The method further includes the steps of providing a non-implanted cardiovertor for providing cardioverting electrical energy, coupling the non-implanted cardiovertor to the first and second electrodes, and causing the cardiovertor to apply the cardioverting electrical energy to the first and second electrodes when the heart of the patient is in need of cardioversion.

The present invention still further provides a method of cardioverting the atria of the heart of a heart surgery patient subsequent to an opened chest heart surgery procedure. The method includes the steps of providing a first lead having a first elongated electrode, the first electrode having a distal end and a proximal end, providing a second lead having a second elongated electrode, the second electrode having a distal end and a proximal end, and following the heart surgery procedure and prior to closing the chest of the patient, releasably anchoring the distal ends of the first and second electrodes to the pericardium. The method further includes the steps of disposing the first electrode along the pericardium adjacent to the right atrium of the heart, disposing the second electrode along the pericardium adjacent to the left atrium of the heart, providing a non-implanted cardioverting means for providing cardioverting electrical energy, coupling the cardioverting means to the first and second electrodes through the first and second leads, and applying the cardioverting electrical energy with the cardioverting means to the first and second electrodes when the atria are in need of cardioversion.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several Figures of which like reference numerals identify identical elements, and wherein:

DETAILED DESCRIPTION OF THE PREFERRED EMBODIMENT

Figure 1:
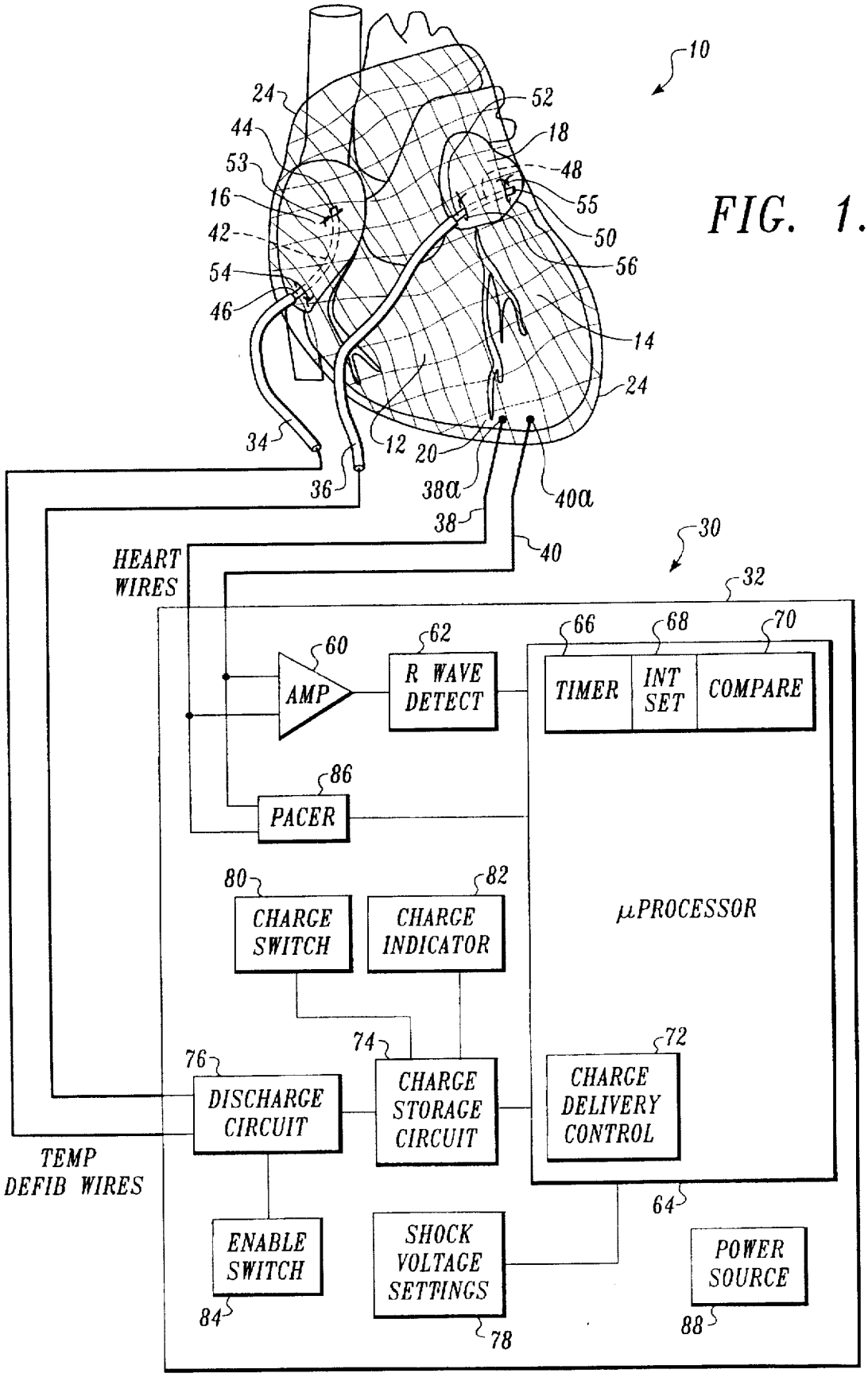
FIG. 1 is a schematic block diagram of a cardioverting system embodying the present invention including an atrial cardiovertor for applying post-surgery cardioverting electrical energy to the atria of a human heart.

Referring now to FIG. 1, it illustrates a cardioverting system 30 embodying the present invention shown in association with a human heart 10 which has undergone surgery and which may require cardioversion of, for example, the atria, during the post-surgery period. The portions of the heart 10 illustrated in FIG. 1 and which will be referred to hereinafter are the right ventricle 12, the left ventricle 14, the right atrium 16, the left atrium 18, and the ventricular myocardium 20. The heart 10, as illustrated, is within the pericardial sac 24 which separates the heart from the lungs (not shown).

The cardioverting system 30 generally includes an external cardiovertor or defibrillator 32 for providing cardioverting electrical energy. This system 30 further includes a first lead 34, a second lead 36, a third lead 38, and a fourth lead 40.

The third and fourth leads 38 and 40 preferably comprise heart wires of the type well known in the art which are releasably attached to the myocardium 20 of the left ventricle 14. The heart wires 38 and 40 have electrodes **38*a* and 40*a* in contact with the myocardium to permit bi-polar sensing of ventricular activations or R waves of the heart 10. As will be seen hereinafter, the heart wires 38 and 40 and their respective electrodes 38*a* and 40*a* may also be used for temporarily pacing the heart 10**.

The first lead 34 includes a first elongated electrode 42 having a distal end 44 and a proximal end 46. The distal end 44 of electrode 42 is releasably anchored to the pericardium 24 by suture 53 which has been given a loose suture knot to permit the electrode 42 to extend along the pericardium 24 and disposed overlying the right atrium 16 while permitting the lead 34 and electrode 42 to be withdrawn from the patient, as by pulling, to disengage the loose suture after the patient has recovered sufficiently so as to no longer require cardioversion.

The electrode 42 may be disposed along either the inner surface or the outer surface of the pericardium. The proximal end 46 of electrode 42 may also be releasably anchored to the pericardium by a suture 54 in a similar manner with a loose suture knot. Alternatively, the electrode 42 may be inserted through the pericardium 24 with the distal end 44 sutured to the pericardium as described above and the proximal end 46 releasably anchored by the point of entry into the pericardium 24.

The second lead 36 similarly includes an elongated electrode 48 having a distal end 50 and a proximal end 52. The distal end 50 of electrode 48 is also releasably anchored to the pericardium 24 by a suture 55 in a manner previously described. The electrode 48 is disposed along the pericardium 24 for overlying the left atrium. Again, the electrode 48 may be disposed along either the inner surface or the outer surface of the pericardium 24. The proximal end 52 of electrode 48 may also be releasably anchored to the pericardium by suture 56 in a manner as previously described.

Figure 2:
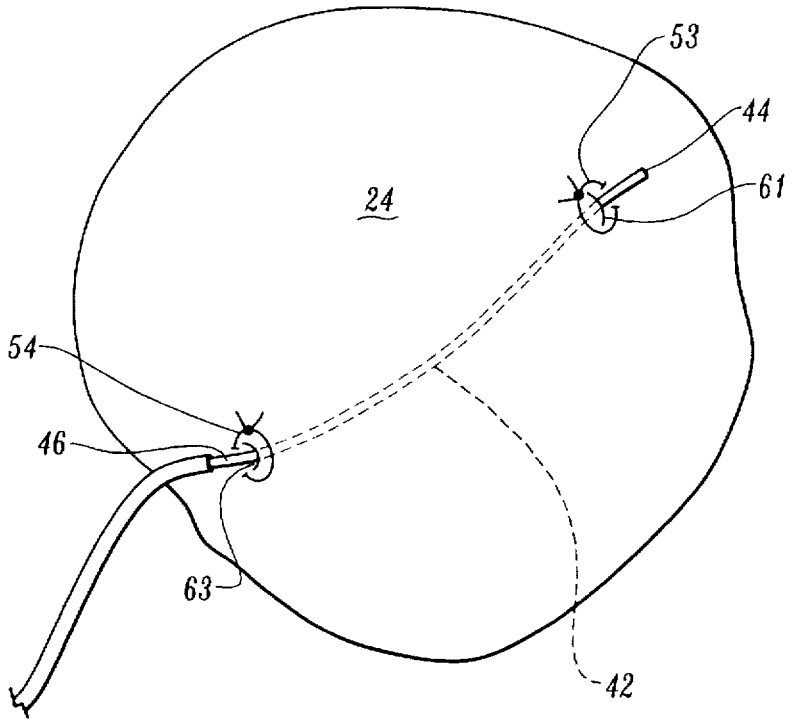
FIG. 2 is a partial plan view illustrating one manner in which the temporary cardioverting electrodes may be releasably anchored to the pericardium of the heart in practicing the present invention.

More specifically, and referring to FIG. 2, one of the electrodes 42 or 48, for example electrode 42, is shown disposed along the inner surface of the pericardium 24. The distal end 44 of electrode 42 is releasably anchored by the loose suture 53 at the point of exit 61 from the pericardium. The proximal end 46 of electrode 42 is also releasably anchored by the loose suture 54 at the point of entry 63 into the pericardium. As previously mentioned, the proximal end 46 of electrode 42 may be releasably anchored by the point of entry 63, in which case, loose suture 54 may be dispensed with.

Figure 3:
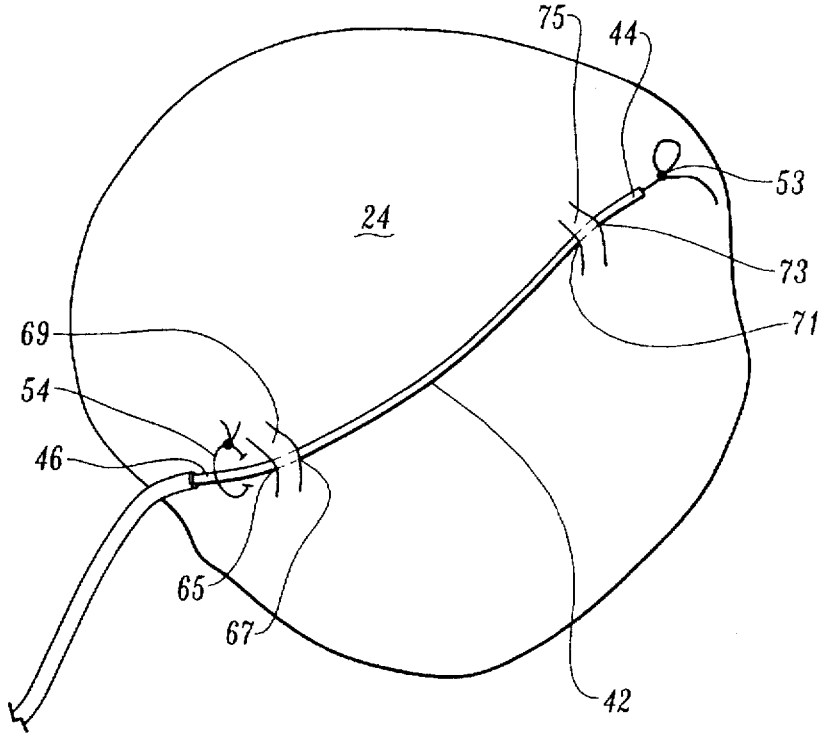
FIG. 3 is another partial plan view illustrating another manner in which the temporary cardioverting electrodes may be releasably anchored to the pericardium in practicing the present invention.

Referring now to FIG. 3, it illustrates one of the electrodes 42 or 48, again for example electrode 42, disposed along the outer surface of the pericardium 24. Here, the electrode 42 is first inserted into the pericardium 24 at a first point of entry 65 and is exited from the pericardium 24 at a first point of exit 67 to form a first pericardial flap 69. The electrode is then extended along the outer surface of the pericardium 24 for substantially its entire length until it reaches a second point of entry 71 into the pericardium 24, and then is exited from the pericardium 24 at a second point of exit 73. This forms a second pericardial flap 75. The distal end 44 of electrode 42 is then releasably anchored to the pericardium with the loose suture 53 at a point beyond the second pericardial flap 75. The second pericardial flap 75, as can be seen in FIG. 3, lends to further assist in the releasable anchoring of distal end 44.

At the proximal end 46 of electrode 42, the first pericardial flap 69 may be used to releasably anchor the proximal end 46. The loose suture 54 may also be employed for this purpose.

The heart wires 38 and 40 may take the form as described in U.S. Pat. No. 4,010,756. The heart wire described in that patent includes a needle-shaped proximal end and a distal end having an electrode with attachment means. The needle shape permits the proximal end to pierce body tissue for bringing the wire proximal end outside of the chest. The needle shape includes a weakened shank portion for breaking off the needle. The shank portion which is left forms a connector for connecting the wire to an external heart stimulating device. The attachment means may include a suture for releasably suturing the distal end electrode. The leads 34 and 36 may be similarly constructed. However, as contemplated by the present invention, certain modifications are preferred. First, while the electrodes of the referenced heart wire are approximately one centimeter in length, it is preferred that the electrodes of leads 34 and 36 be approximately six centimeters in length. Further, it is preferred that the electrodes 42 and 48 be flexible to permit the electrodes to conform to the shape or contour of the pericardium and the heart to assure continuous electrical contact between the electrode and the body tissue. In addition, it is preferred that the impedance of the leads 42 and 48 be made substantially lower than the impedance of prior art heart wires. Such wires may have an impedance of fifteen ohms or more whereas an impedance on the order of one ohm is preferred for leads 34 and 36. Such a low impedance may be achieved by forming the conductor of leads 34 and 36 with stranded wire of stainless steel and providing the conductor with a continuous central core of silver. The conductor may then be provided with insulation up to the electrodes.

Referring again to FIG. 1, the cardiovertor 32 includes a sense amplifier 60 and an R wave detector 62. The output of the sense amplifier 60 is coupled to the R wave detector 62. The sense amplifier 60 and the R wave detector 62 form a detecting means which, together with the heart wires 38 and 40 to which sense amplifier 60 is coupled, senses ventricular activations or R waves of the heart. The R wave detector 62 is of the type well known in the art which provides an output pulse upon the occurrence of an R wave being sensed during a cardiac cycle of the heart.

The cardiovertor 32 further includes a microprocessor 64. The implementation of the microprocessor 64 in accordance with this embodiment of the present invention results in a plurality of functional stages. The stages include a timer 66, an interval set stage 68, a comparator stage 70, and a charge delivery and energy control stage 72.

The microprocessor 64 is arranged to operate in conjunction with a memory (not shown) which may be coupled to the microprocessor by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and conveys the data to the memory over the multiple-bit data bus. During a read operation, the microprocessor 64 obtains data from the memory at the storage locations identified by the multiple-bit addresses provided over the address bus and receives the data from the memory over the bi-directional data bus.

The cardiovertor 32 further includes a charger and storage capacitor circuit 74 of the type well known in the art which charges a storage capacitor to a peak voltage level determined by a voltage setting control 78 and a discharge circuit 76 for discharging the storage capacitor within circuit 74 for a predetermined time period to provide a controlled discharge output of electrical energy when enabled by an enable switch 84. To that end, the discharge circuit 76 is coupled to the first electrode 42 of the first lead 34 and the second electrode 48.of the second lead 36 for applying the cardioverting electrical energy to the atria.

Associated with the charger and delivery control 72 is a manually operated charge switch 80 and a charge indicator 82. When it is desired to charge the capacitor of circuit 74, the switch 80 is actuated. When the capacitor is charged to a desired peak voltage selected with setting control 78, the indicator, such as an LED, will provide a suitable indication.

The defibrillator 32 further includes a pacemaker circuit 86 of the type well known in the art for providing pacing electrical energy pulses. The pacemaker circuit is preferably operable in a demand mode (VVI) and is coupled to the heart wires 38 and 40 for providing demand pacing of the heart. Alternatively, the pacer 86 may be operative in a dual chamber pacing mode, such as the DDD mode. This however would require another pair of heart wires to be attached to one of the atria.

Lastly, the cardiovertor 32 includes a power source 88 for providing power to the electrical components of the atrial cardiovertor 32. The power source 88 may be an AC power supply since the cardiovertor 32 is intended for external use, or it may be a battery if portability of the cardiovertor 32 is preferred.

After the heart surgery is completed, the heart wires 38 and 40 and leads 34 and 36 are attached to the heart as previously described, and the patient's chest is closed, the cardiovertor 32 is coupled to the heart wires 38 and 40 and leads 34 and 36 as illustrated. The pacer 86 is then activated to provide demand pacing and the sense amplifier 60 and the R wave detector 62 begin detecting the occurrence of ventricular activations of the heart to support the demand pacing modality. During at least the initial recovery period in which the post-heart surgery patient may experience an arrhythmia such as atrial fibrillation, the patient will be coupled to an external ECG monitor by which such arrhythmias may be detected. If an atrial arrhythmia is detected, a desired peak voltage from which cardioversion is to begin is manually selected with setting control 78. The charger and delivery control switch 80 is then manually actuated. This causes the storage capacitor of circuit 74 to begin being charged. When the voltage on the capacitor reaches the desired peak voltage, the indicator 82 will indicate that the capacitor is fully charged. Next, the enable switch 84 is manually actuated to condition the discharge circuit 76 to initiate the discharge of the storage capacitor within circuit 74 into leads 34 and 36 and electrodes 42 and 48 at the appropriate time to cardiovert the atria The discharge circuit 76 initiates the discharge of the cardioverting electrical energy under the control of the charger and delivery control 72.

The discharge is preferably synchronized with an R wave, detected by sense amplifier 60 and the R wave detector 62, which establishes the first R to R interval falling between a minimum interval and a maximum interval previously set in the interval set stage 68. The timer 66 determines the time between immediately successive detected R waves. After the enable switch is actuated and with each detected R wave, microprocessor 64 interrogates the timer 66 for the time between the last immediately successive ventricular activations of the heart 10.

The compare stage 70 of the microprocessor then determines if the time between the last two immediately successive ventricular activations is greater than the minimum time interval and less than the maximum time interval. As soon as the microprocessor 64 finds an R to R interval greater than the preselected minimum time interval ($I_{min}$) and less than the preselected maximum time interval ($I_{max}$), the charge delivery control stage 72 of microprocessor 64 causes the discharge circuit 76 to immediately initiate the discharge of the electrical energy stored in the storage capacitor of circuit 74 for applying the cardioverting electrical energy to electrodes 42 and 48 and thus to the atria 16 and 18 of the heart 10. Since the microprocessor 64 is able to process the R to R interval data very quickly after the occurrence of each detected ventricular activation, the discharge circuit 76 will apply the cardioverting electrical energy to the atria of the heart substantially coincident or in synchronism with the detected ventricular activation establishing the R to R interval satisfying the discharge criteria.

The minimum and maximum R to R intervals may also be selected automatically as fully disclosed in U.S. Pat. No. 5,207,219 which is assigned to the assignee of the present invention and incorporated herein by reference. As fully disclosed therein, the R to R interval timing prior to cardioversion assures safe cardioversion by avoiding the application of the cardioverting energy when the heart may be vulnerable to induced ventricular fibrillation.

The cardioverting electrical energy is preferably applied for a fixed time period using a time symmetrical biphasic waveform. Because the electrodes 42 and 48 are either on the inner surface or outer surface of the pericardium, energies between only one and five joules, depending upon the patient, are required for successful cardioversion. These energy levels are much less than the energy levels of fifty to three hundred and sixty joules generally required for external cardioversion.

As can thus be seen from the foregoing, the post-surgery cardioverting system and method of the present invention satisfies a long felt need in the art for safe and effective treatment of post-heart surgery fibrillation. The system and method of the present invention avoids the need for drug therapy. Further, the option of external cardioversion with high energy requirements no longer need be considered. As a result, the post-heart surgery patient suffering from atrial fibrillation is no longer required to endure the effects of such a condition. The fibrillation, by virtue of the present invention, may be effectively terminated without prolonging the patient's recovery. When the patient has sufficiently recovered so as to no longer require pacing or cardioversion, the heart wires and cardioverting leads may be pulled out of the patient's chest.

While a particular embodiment of the present invention has been shown and described, modifications may be made. For example, the system and method of the present invention may also be utilized to advantage to terminate ventricular tachycardia or even ventricular fibrillation during the post-surgery period. In such an application, the elongated electrodes would be disposed along the pericardium to overlie the ventricles. The electrodes may be releasably anchored to the pericardium as disclosed herein to enable the electrodes to be removed from the patient by pulling on the leads to which the electrodes are attached. Hence, it is therefore intended in the appended claims to cover all such changes and modifications which fall within the true spirit and scope of the invention.

What is claimed is:

1. A post-surgical cardioverting system for applying cardioverting electrical energy to the heart of a post-surgical heart patient, said system comprising:

a first lead including a first elongated electrode, said first electrode having a proximal end and a distal end;

a second lead including a second elongated electrode, said second electrode having a proximal end and a distal end;

first anchor means for releasably anchoring the distal ends of said first and second electrodes to body tissue external to but in close proximity to the heart beneath the skin of the patient to dispose said first and second electrodes in electrical contact with the heart; and non-implantable cardioverting means coupled to said first and second leads for applying said cardioverting electrical energy to said first and second electrodes.

2. A system as defined in claim 1 wherein said first anchor means comprises suture means for releasably suturing the distal ends of said first and second electrodes to said body tissue external to but in close proximity to the heart.

3. A system as defined in claim 1 further including second anchor means for releasably anchoring the proximal ends of said first and second electrodes to body tissue external to but in close proximity to the heart beneath the skin of the patient.

4. A system as defined in claim 3 wherein said second anchor means comprises suture means for releasably suturing the proximal ends of said first and second electrodes to said body tissue external to but in close proximity to the heart.

5. A system as defined in claim 1 further including sensing means for sensing R waves of the heart, and wherein said cardioverting means is coupled to said sensing means and responsive to R waves sensed by said sensing means for applying said cardioverting electrical energy to said first and second electrodes in timed relation to a sensed R wave.

6. A system as defined in claim 5 wherein said cardioverting means is further responsive to said sensed R waves for applying said cardioverting electrical energy to said first and second electrodes when the time between immediately successive R waves is greater than a preselected minimum time interval.

7. A system as defined in claim 5 wherein said sensing means comprises third and fourth electrodes and attachment means for releasably attaching said third and fourth electrodes to a ventricle of the heart.

8. A system as defined in claim 7 wherein said cardioverting means further includes pacing means coupled to said third and fourth electrodes for applying pacing electrical energy pulses to said third and fourth electrodes.

9. A system as defined in claim 1 wherein said first and second elongated electrodes each have a length dimension for extending across a substantial portion of a respective chamber of the heart.

10. A system as defined in claim 1 wherein said first and second elongated electrodes each have a length dimension for extending across a substantial portion of the right and left atria respectively.

11. A system as defined in claim 1 wherein said first and second elongated electrodes each have a length dimension of approximately six centimeters.

12. A system as defined in claim 1 wherein said first and second leads each have an impedance of one ohm or less.

13. A method of cardioverting the heart of a heart surgery patient subsequent to a heart surgery procedure, said method comprising the steps of:

providing a first lead having a first elongated electrode, said first electrode having a distal end and a proximal end;

providing a second lead having a second elongated electrode, said second electrode having a distal end and a proximal end;

following said heart surgery procedure and before closing the chest of the patient, releasably anchoring said distal ends of said first and second electrodes to body tissue external to but in close proximity to the heart beneath the skin of the patient to dispose said first and second electrodes in electrical contact with the heart;

providing a non-implanted cardioverting means for providing cardioverting electrical energy;

coupling said non-implanted cardioverting means to said first and second electrodes; and causing said cardioverting means to apply said cardioverting electrical energy to said first and second electrodes when the heart of the patient is in need of cardioversion.

14. A method as defined in claim 13 wherein said anchoring step includes releasably suturing said distal ends of said first and second electrodes to body tissue external to but in close proximity to the heart beneath the skin of the patient.

15. A method as defined in claim 13 wherein said anchoring step includes releasably anchoring said distal ends of said first and second electrodes to the pericardium.

16. A method as defined in claim 15 wherein said anchoring step includes disposing said first and second electrodes along the inside of the pericardium.

17. A method as defined in claim 15 wherein said anchoring step includes disposing said first and second electrodes along the outside of the pericardium.

18. A method as defined in claim 15 wherein said anchoring step includes releasably anchoring said proximal ends of said first and second electrodes to the pericardium.

19. A method as defined in claim 18 wherein said anchoring step includes releasably suturing said distal ends and said proximal ends of said first and second electrodes to the pericardium.

20. A method as defined in claim 13 wherein said method is for applying cardioverting electrical energy to the atria of the heart and wherein said anchoring step includes disposing said first electrode to overlie the right atrium and disposing said second electrode to overlie the left atrium.

21. A method as defined in claim 20 wherein said anchoring step includes releasably anchoring said distal ends of said first and second electrodes to the pericardium, disposing said first electrode along the pericardium to overlie the right atrium, and disposing said second electrode along the pericardium to overlie the left atrium.

22. A method as defined in claim 21 wherein said anchoring step includes disposing said first and second electrodes along the inside of the pericardium.

23. A method as defined in claim 21 wherein said anchoring step includes disposing said first and second electrodes along the outside of the pericardium.

24. A method as defined in claim 21 wherein said anchoring step includes releasably anchoring said proximal ends of said first and second electrodes to the pericardium.

25. A method as defined in claim 24 wherein said anchoring step includes releasably suturing said distal ends and said proximal ends of said first and second electrodes to the pericardium.

26. A method as defined in claim 13 including the further steps of;

providing sensing means for sensing R waves of the heart, sensing R waves of the heart with said sensing means; and causing said cardioverting means to apply said cardioverting electrical energy to said first and second electrodes in timed relation to a sensed R wave.

27. A method as defined in claim 26 wherein said last recited causing step includes causing said cardioverting means to apply said cardioverting electrical energy to said first and second electrodes when the time between immediately successive sensed R waves is greater than a preselected minimum time period.

28. A method as defined in claim 26 wherein said step of providing said sensing means includes providing third and fourth electrodes, releasably attaching said third and fourth electrodes to a ventricle of the heart, and coupling said third and fourth electrodes to said cardioverting means.

29. A method as defined in claim 28 including the further steps of providing said cardioverting means with pacing means for providing pacing electrical energy pulses, coupling said pacing means to said third and fourth electrodes, and causing said pacing means to apply said pacing electrical energy pulses to said third and fourth electrodes.

30. A method of cardioverting the atria of the heart of a heart surgery patient subsequent to an opened chest heart surgery procedure, said method comprising the steps of:

providing a first lead having a first elongated electrode, said first electrode having a distal end and a proximal end;

providing a second lead having a second elongated electrode, said second electrode having a distal end and a proximal end;

following said heart surgery procedure and prior to closing the chest of the patient, releasably anchoring said distal ends of said first and second electrodes to the pericardium;

disposing said first electrode along the pericardium adjacent to the right atrium of the heart;

disposing said second electrode along the pericardium adjacent to the left atrium of the heart;

providing a non-implanted cardioverting means for providing cardioverting electrical energy;

coupling said cardioverting means to said first and second electrodes through said first and second leads; and applying said cardioverting electrical energy with said cardioverting means to said first and second electrodes when the atria are in need of cardioversion.

31. A post-surgical defibrillating system for applying defibrillating electrical energy to the heart of a post-surgical heart patient, said system comprising:

a first lead including a first elongated electrode, said first electrode having a proximal end and a distal end;

a second lead including a second elongated electrode, said second electrode having a proximal end and a distal end;

first anchor means for releasably anchoring the distal ends of said first and second electrodes to body tissue external to but in close proximity to the heart beneath the skin of the patient to dispose said first and second electrodes in electrical contact with the heart; and non-implantable defibrillator coupled to said first and second leads for applying said defibrillating electrical energy to said first and second electrodes.

*32. A post-surgical cardioverting system for applying cardioverting electrical energy to the heart of a post-surgical heart patient, said system comprising:*

*a first lead including a first elongated electrode, said first electrode having a proximal end and a distal end;*

*a second lead including a second elongated electrode, said second electrode having a proximal end and a distal end;*

*said first and second electrodes adapted to be in electrical contact with the heart;*

*at least one anchor at the distal end of said first and second electrodes releasably connected beneath the skin of the patient; and*

*a non-implantable cardioverter electrically coupled for cardioversion by said first and second leads to the heart.*

*33. A system as defined in claim 32 in which said anchor is adapted to be connected to body tissue external to but in close proximity to the heart beneath the skin of the patient.*

*34. A system as defined in claim 32 in which said anchor is adapted to be attached to the pericardium of the heart.*

*35. A system as described in claim 32 in which said anchor is a suture.*

*36. A system as defined in claim 32 in which said anchor is a suture adapted to be attached to the pericardium of the heart.*

*37. A post-surgical cardioverting system for applying cardioverting electrical energy to the heart of a post-surgical heart patient, said system comprising:*

*a first lead including a first elongated electrode;*

*a second lead including a second elongated electrode;*

*anchor means for releasably anchoring the first and second electrodes to body tissue beneath the skin of the patient to dispose said first and second electrodes in electrical contact with the heart; and*

*non-implantable cardioverting means coupled to said first and second leads for applying said cardioverting electrical energy to said first and second electrodes for cardioversion of the heart.*

*38. A system as defined in claim 37 in which said anchor means is adapted to be connected to body tissue external to but in close proximity to the heart beneath the skin of the patient.*

*39. A system as defined in claim 37 in which said anchor means is adapted to be attached to the pericardium of the heart.*

*40. A system as described in claim 37 in which said anchor means is a suture.*

*41. A system as described in claim 37 in which said anchor means is a suture adapted to be attached to the pericardium of the heart.*

*42. A method of cardioverting the heart of a heart surgery patient subsequent to a heart surgery procedure, said method comprising the steps of:*

*providing a first lead having a first elongated electrode, said first electrode having a distal end and a proximal end;*

*providing a second lead having a second elongated electrode, said second electrode having a distal end and a proximal end;*

*placing said first and second electrodes in electrical contact with the heart;*

*following said heart surgery procedure, releasable anchoring said distal ends of said first and second electrodes to body tissue beneath the skin of the patient;*

*providing a non-implanted cardiovertor for providing cardioverting electrical energy;*

*coupling said non-implantable cardioverting means to said first and second electrodes; and*

*causing said cardioverting means to apply said cardioverting electrical energy to said first and second electrodes for cardioversion of the heart.*

*43. A method as defined in claim 42 wherein said anchoring step includes anchoring said first and second electrodes to body tissue external to but in close proximity to the heart.*

*44. A method as defined in claim 42 wherein said anchoring step includes anchoring said first and second electrodes to the pericardium of the heart.*

*45. A method as defined in claim 42 wherein said anchoring step includes suturing.*

*46. A method as defined in claim 42 wherein said anchoring step includes suturing the first and second electrodes to the pericardium of the heart.*

*47. A method of cardioverting the heart of a heart surgery patient subsequent to a heart surgery procedure, said method comprising the steps of:*

*providing a first lead having a first elongated electrode;*

*providing a second lead having a second elongated electrode;*

*following said heart surgery procedure releasably disposing said first and second electrodes in electrical contact with the heart;*

*providing a non-implanted cardioverting means for providing cardioverting electrical energy;*

*coupling said non-implanted cardiovertor to said first and second electrodes; and*

*causing said cardioverting means to apply said cardioverting electrical energy to said first and second electrodes for cardioversion of the heart.*

*48. A method as defined in claim 47 wherein said disposing step includes releasably anchoring said first and second electrodes to body tissue external to but in close proximity to the heart.*

*49. A method as defined in claim 47 wherein said disposing step includes releasably anchoring said first and second electrodes to the pericardium of the heart.*

*50. A method as defined in claim 47 wherein said disposing step includes suturing.*

*51. A method as defined in claim 47 wherein said anchoring step includes releasably suturing the first and second electrodes to the pericardium of the heart.*

* * * * *